United States Patent
Faux

(10) Patent No.: US 9,662,155 B2
(45) Date of Patent: May 30, 2017

(54) SURGICAL SYSTEMS AND METHODS FOR ASSEMBLING AND FUSING BONES

(71) Applicant: FOOTMIND, INC., Alpine, UT (US)

(72) Inventor: Jonathan Robert Faux, Provo, UT (US)

(73) Assignee: FusioNX, Sarl, Luxembourg (LU)

(*) Notice: Subject to any disclaimer, the term of this patent is extended or adjusted under 35 U.S.C. 154(b) by 0 days.

(21) Appl. No.: 14/536,311

(22) Filed: Nov. 7, 2014

(65) Prior Publication Data
US 2015/0073412 A1  Mar. 12, 2015

Related U.S. Application Data

(63) Continuation of application No. PCT/US2014/048146, filed on Jul. 25, 2014.
(Continued)

(51) Int. Cl.
*A61B 17/72* (2006.01)
*A61B 17/16* (2006.01)
(Continued)

(52) U.S. Cl.
CPC ...... *A61B 17/7291* (2013.01); *A61B 17/1615* (2013.01); *A61B 17/1682* (2013.01);
(Continued)

(58) Field of Classification Search
CPC ............ A61B 17/1615; A61B 17/1617; A61B 17/1637; A61B 17/1662; A61B 17/72;
(Continued)

(56) References Cited

U.S. PATENT DOCUMENTS

| 4,969,909 A * | 11/1990 | Barouk | A61B 17/72 606/62 |
|---|---|---|---|
| 2007/0288097 A1* | 12/2007 | Hurowitz | A61B 17/72 623/47 |

(Continued)

FOREIGN PATENT DOCUMENTS

| RU | 2176485 C2 | 12/2001 |
|---|---|---|
| RU | 2202967 C2 | 4/2003 |
| RU | 2313370 C2 | 1/2007 |

OTHER PUBLICATIONS

Dr. Luke D. Cicchinelli, DPM, "Trim-It Drill Pin(TM) for Hammertoe Surgery: Part 2," Mar. 20, 2013 [retrieved online Sep. 15, 2014] <URL://http://footandanklefixation.com/experience/trim-it-drill-pin-for-hammertoe-surgery-part-2/>.
(Continued)

*Primary Examiner* — Eduardo C Robert
*Assistant Examiner* — Julianna N Harvey
(74) *Attorney, Agent, or Firm* — Durham Jones & Pinegar, P.C.

(57) ABSTRACT

A surgical system for use in correcting hammer toe or otherwise straightening toes or fusing other bones to one another includes a male drill bit and a female drill bit, as well as an absorbable pin. The male and female drill bits are configured to define complementary features from opposed, or facing, ends of bones that are to be fused to one another. The male and female drill bits may also be configured to define channels through the lengths of the bones that are to be fused to one another, with the channels being configured to align and define a continuous channel through the bones when they are assembled. The absorbable pin, which may be absorbed by a subject's body over time, is configured to be
(Continued)

positioned in the continuous channel, and may hold the bones in an assembled relationship before and while they fuse to one another.

20 Claims, 1 Drawing Sheet

Related U.S. Application Data

(60) Provisional application No. 61/860,257, filed on Jul. 31, 2013.

(51) Int. Cl.
*A61B 17/00* (2006.01)
*A61B 17/56* (2006.01)

(52) U.S. Cl.
CPC *A61B 17/7233* (2013.01); *A61B 2017/00004* (2013.01); *A61B 2017/564* (2013.01)

(58) Field of Classification Search
CPC ............ A61B 17/7208; A61B 17/1686; A61B 17/1682; A61B 17/7291; A61B 17/7216; A61B 17/7225
See application file for complete search history.

(56) References Cited

U.S. PATENT DOCUMENTS

| | | | |
|---|---|---|---|
| 2008/0086139 A1* | 4/2008 | Bourke | A61B 17/68 606/270 |
| 2011/0004255 A1* | 1/2011 | Weiner | A61B 17/1682 606/301 |
| 2011/0301653 A1 | 12/2011 | Reed et al. | |
| 2014/0257509 A1* | 9/2014 | Dacosta | A61F 2/4225 623/21.19 |

OTHER PUBLICATIONS

Russian Federation as the International Searching Authority, "International Search Report and Written Opinion," mailed Oct. 16, 2014, in related PCT application No. PCT/US2014/048146.

\* cited by examiner

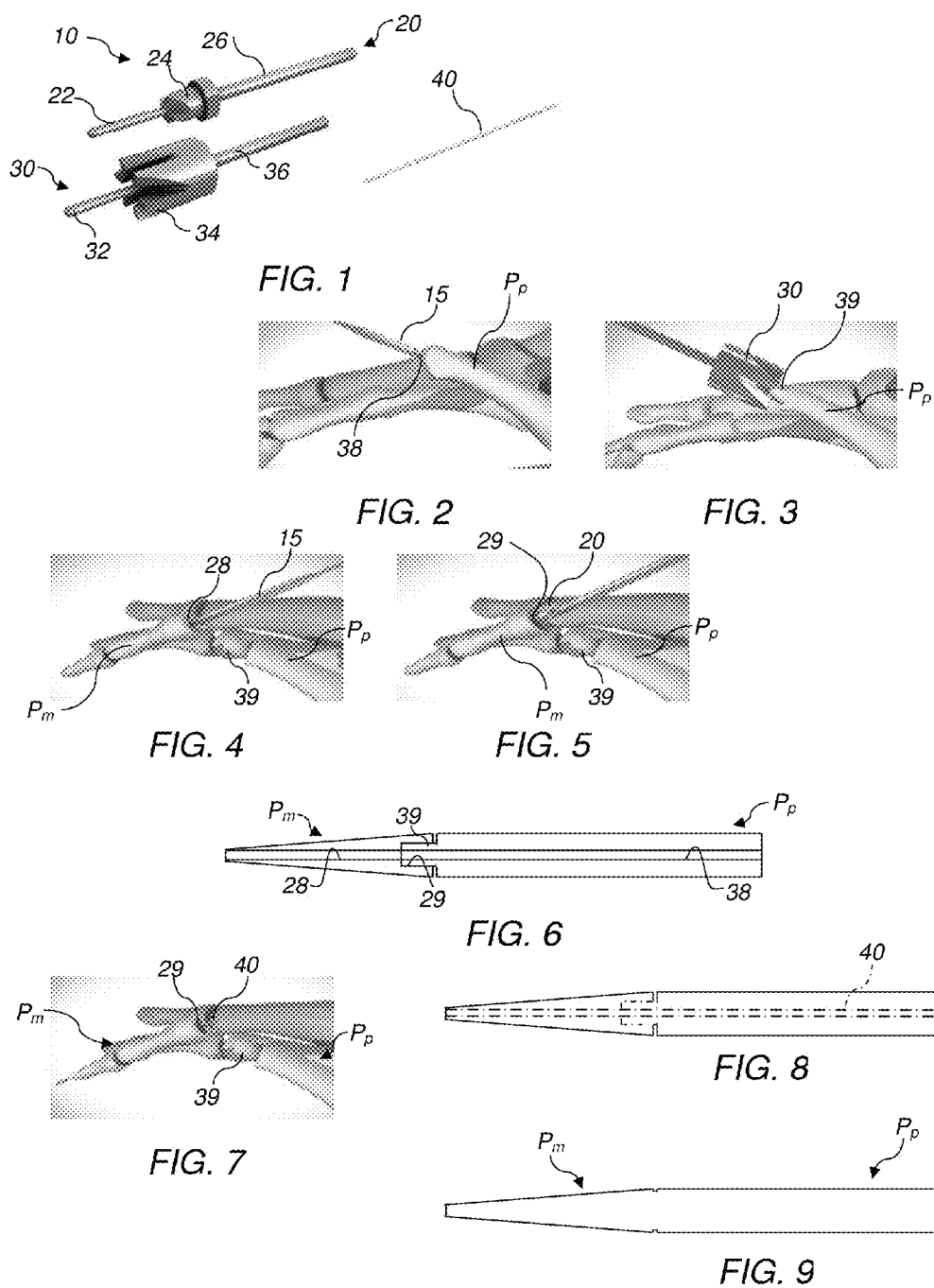

SURGICAL SYSTEMS AND METHODS FOR ASSEMBLING AND FUSING BONES

CROSS-REFERENCE TO RELATED APPLICATIONS

This application is a continuation of International Patent Application No. PCT/US2014/048146, which was filed pursuant to the Patent Cooperation Treaty on Jul. 25, 2014, titled SURGICAL SYSTEMS AND METHODS FOR ASSEMBLING AND FUSING BONES (hereafter "the '146 PCT Application"). The '146 PCT Application claims the benefit of the Jul. 13, 2013, filing date of U.S. Provisional Patent Application No. 61/860,257, titled SURGICAL SYSTEMS AND METHODS FOR ASSEMBLING AND FUSING BONES ("the '257 Provisional Application"). The entire disclosure of each of the foregoing patent applications is hereby incorporated herein.

TECHNICAL FIELD

This disclosure relates generally to surgical tools and systems for adjusting the orientations (e.g., straightening, etc.) bones at joints and, more specifically, to surgical systems that include drills and pins that are configured to shape the adjacent ends of bones (e.g., phalanges, etc.) that form part of a joint to enable the adjacent ends of the bones to fit together in a desired assembled relationship and to enable the adjacent ends of the bones to fuse to one another. In particular, the disclosed surgical tools and systems are useful for correcting hammer toe or other digital deformities by reshaping a proximal interphalangeal joint in a manner that enables the bones to be assembled in a normal orientation (e.g., a substantially straight relationship, a natural angle, etc.) and to fuse the adjacent bones together in that more normal orientation. Even more specifically, this disclosure relates to pins that are formed from so-called "absorbable" materials, to surgical systems with absorbable pins for straightening bones (e.g., for correcting hammer toe, other phalangeal deformities, etc.) and to methods that involve the use of absorbable pins in adjusting the orientations of (e.g., straightening, etc.) bones.

RELATED ART

Hammer toe occurs when a toe assumes an involuntarily bent orientation at the joint located closes to the end of the toe, which is known as a proximal interphalangeal joint. When hammer toes are still flexible (i.e., they can be bent to a normal, somewhat straight orientation), they can often be treated without surgery. Treatment of rigid hammer toes, in contrast, typically requires surgery, as the tendons have usually tightened too much and the proximal interphalangeal joint has become immobile and misaligned.

Corrective surgery for hammer toe and similar conditions typically includes shaping the ends of the bones on each side to the affected proximal interphalangeal joint so that the bones will fit together in a normal (or, at least, more normal) orientation, and inserting a pin through the centers of the shaped bones to hold them in the desired relationship as the body reacts to trauma from the procedure by (typically) fusing the assembled ends of the bones together. When the bones are fused—which usually does not occur until after (an) incision(s) through the skin of the affected toe (has) have substantially healed, a second surgical procedure is usually be performed to remove the pin from the toe. The second surgical procedure is undesirable for a number of reasons, including the additional time required for traveling to a facility (e.g., a doctor's office, a clinic, a hospital, etc.) where the second surgical procedure will be performed, the additional time needed for the healthcare professional(s) to prepare for, perform and close the second surgical procedure, the additional pain that typically follows the second surgical procedure, the additional time it takes for the body to heal following the procedure and the increased likelihood of complications (e.g., infection, adverse drug reaction, etc.) presented by the second surgical procedure.

SUMMARY

This disclosure relates to a variety of aspects, including, without limitation, systems, kits and methods, for adjusting the orientations of bones (e.g., substantially straightening bones, etc.). The systems, kits and methods may be useful for a variety of procedures, including, without limitation, procedures in which a joint between adjacent bones is deformed in a manner that positions the adjacent bones in an undesired orientation relative to one another. In its various aspects, the disclosure relates to systems, kits and methods for adjusting the orientation of a bone or pair of adjacent bones with a single surgical procedure. While much of the disclosure focuses use of the disclosed systems in procedures for correcting hammer toe and similar deformities, use of a system according to this disclosure should not necessarily be limited to procedures for orienting phalanges in more normal orientations (e.g., a substantially straight orientation, an orientation with a bend (i.e., an angle) that is typically present in a pair of adjacent bones that have formed normally and that lack deformities (in the bones or in a joint between the adjacent bones), etc.).

A system that incorporates teachings of this disclosure includes one or more elements that are configured to define complementary, mutually engaging features at ends of two bones that are to be fused to one another, as well as an absorbable pin, which may help maintain an assembled relationship between two bones while they heal in a manner that fuses them together. In some embodiments, the ends of the two bones that are to be assembled with each other may comprise the ends of bones that previously formed a joint (e.g., an interphalangeal joint, etc.) and, thus, that faced or opposed one another. Accordingly, the ends of the bones that are to be assembled with and fused to one another may be referred to herein as "opposed ends." The elements that are configured to define complementary, mutually engaging features at the opposed ends of adjacent bones may comprise a male drill bit and a female drill bit. The female drill bit may define a protruding feature at the end of one of the adjacent bones, while the male drill bit may be configured to define a complementary recess, or receptacle, in the end of the other of the adjacent bones. The male and female drill bits may also be configured to define channels through the lengths of the bones that are to be fused to one another, with the channels being configured to align and define a continuous channel through the bones when they are assembled. Alternatively, each of the male and female drill bits may include a guide configured to be received by a channel (which may be formed by a separated, standard drill bit), or guide hole, which holds or the male or female drill bit in place or stabilizes the male or female drill bit while it defines its corresponding feature at the end of a bone.

The absorbable pin may be configured to be positioned in the continuous channel, and may hold the bones in an assembled relationship before and while they fuse to one another. An "absorbable" material is a material that, over time, is dissolved by a subject's body. The absorbable material may include or be used in conjunction with a material that stimulates bone growth, or an "osteogenic" material. An absorbable pin may be configured to provide structural support to a bone until two or more bones or two or more pieces of bones that have been assembled with one another have healed, or fused, sufficiently to define a bone with sufficient strength to support itself in normal use. In some embodiments, a pin formed from an absorbable material may be configured to completely dissolve within weeks or months (e.g., two months, four months, etc.) after it has been introduced into the body of a subject. By being formed from an absorbable material, an absorbable pin may not need to be surgically removed from the body, eliminating the need for a follow-up surgical procedure.

A kit for toe straightening surgery may include a male drill bit, a female drill bit and a plurality of absorbable pin, each of which may have any of the configurations or characteristics disclosed herein. In a specific embodiment, the male drill bit and the female drill bit may be reusable. A reusable male drill bit and female drill bit may be configured to be sterilized in a suitable manner. When the male drill bit and the female drill bit are reusable, the plurality of absorbable pins may be used in procedures on different toes of the same patient and/or for separate procedures on different patients. In other embodiments, the additional absorbable pin(s) may be provided in the event that another pin fails before or while it is inserted into a channel that extends through at least portions of two or more aligned bones or bone pieces.

A method for straightening bones, such as a phalange (i.e., bones in a finger or toe) across an interphalangeal joint, includes separating adjacent, relatively straight bones from one another at a joint. A guide hole may then be formed in the newly exposed end of each bone that has been separated. The previously joined, or opposed, ends of the bones may be imparted with complementary, or mating, features. Without limitation, the end of one bone, or a first bone, of the adjacent bones may be imparted with a female configuration or feature, or a recess or receptacle (e.g., by a male drill bit, etc.), while the opposed end of the other bone, or a second bone, of the adjacent bones may be imparted with a male configuration, or a protruding feature (e.g., by a female drill bit, etc.), that is configured to mate with the female configuration at the end of the first bone. The complementary features at the opposed ends of the adjacent bones may be assembled with, and optionally engage, one another. As the complementary features are assembled, the adjacent bones are also assembled in a desired (e.g., substantially straight, etc.) relationship.

In some embodiments, a channel may be defined through at least a portion of the length of each of the adjacent bones. In embodiments where guide holes are formed, each guide hole may serve as all or part of the channel though its respective bone. A channel may include a junction end that opens to an opposed end of one of the adjacent bones and extend partially into that bone to a terminal end that terminates within the bone. Alternatively, a channel may include a junction end that opens to an opposed end of one of the adjacent bones and extend partially or completely through that bone to an outer end that opens to another surface of the bone (e.g., an opposite end of the bone, a medially located surface of the bone, etc.). Each channel may be defined while one of the complementary features is defined at an opposed end of one of the adjacent bone (e.g., by an elongated bit centered relative to the male drill bit or the female drill bit, etc.). Alternatively, each channel may be formed in a bone separately from definition of the complementary feature at the opposed end of that bone. The channels may be positioned to align with each other when the complementary features at the opposed ends of the adjacent bones, and, thus, the adjacent bones themselves, are assembled with and optionally engage one another. Thus, when the adjacent bones are assembled, the channels in the adjacent bones may define a continuous channel through the adjacent bones.

In embodiments where channels are defined at least partially through the adjacent bones, an absorbable pin may be inserted into the channels, across a junction between the channels in the adjacent bones. The use of an absorbable pin may structurally reinforce, or support, the newly reassembled bones as they fuse to each other and, thus, as they heal. In embodiments where the absorbable pin includes an osteogenic material, use of the pin may expedite or otherwise enhance fusion of the adjacent bones and, thus, accelerate healing of a bone that has been straightened or otherwise had its orientation adjusted. Insertion of the absorbable pin may occur before and during assembly of the adjacent bones with one another or, in embodiments where an outer end of a channel opens to a surface of the bone (e.g., to a distal end of a distal-most of the adjacent bones or at another location on a surface of the bone), the absorbable pin may be inserted after the adjacent bones have been assembled.

When an absorbable pin is used, a follow-up pin-removal procedure (i.e., a surgical procedure in which an incision is made in skin adjacent to an outer end of a channel through one of the adjacent bones to remove the pin from a continuous channel that extends at least partially through the adjacent bones) will typically be unnecessary. Thus, use of an absorbable may eliminate the need for a follow-up surgical procedure.

Because a follow-up pin-removal procedure is unnecessary, a method for fusing two bones or two pieces of bones may consist essentially of or even consist of: accessing two adjacent bones or bone pieces; separating the adjacent bones or bone pieces from one another; defining complementary, or mating, features at the opposed, or adjacent, ends of the bones or bone pieces; defining a channel that extends into the end of each of the bones or bone pieces; placing the bones or bone pieces in an assembled relationship while causing the complementary features to engage each other; inserting an absorbable pin into the channels, with the absorbable pin ultimately crossing an interface between the two bones or bone pieces; and closing the incision and/or wound by which the bones or bone pieces were exposed.

Other aspects, as well as features and advantages of various aspects, of the disclosed subject matter will become apparent to those of ordinary skill in the art through consideration of the ensuing description, the accompanying drawings and the appended claims.

BRIEF DESCRIPTION OF THE DRAWINGS

In the drawings:

FIG. 1 provides a perspective view of various elements of a surgical system for correcting hammer toe or otherwise correcting the orientation of a digit or a bone;

FIGS. 2 and 3 illustrate use of a female drill to define a protruding feature on an end of a first bone;

FIGS. 4 and 5 illustrate use of a male drill to define a recess in an end of a second bone;

FIG. 6 is a cross-sectional representation of an assembled relationship of the bones of FIGS. 3 and 5;

FIG. 7 shows an embodiment of the insertion of an absorbable pin into a continuous channel extending through the bones of FIG. 6;

FIG. 8 depicts partial absorption of the absorbable pin; and

FIG. 9 depicts complete absorption of the absorbable pin.

DETAILED DESCRIPTION

With reference to FIG. 1, various elements of an embodiment of a surgical system 10, or kit, are illustrated. The surgical system 10 may be configured to position a bone or, more specifically, a pair of adjacent bones, in a desired orientation. In a specific, but non-limiting, embodiment, the surgical system may be configured to correct the orientation of a toe with a deformed interphalangeal joint, such as occurs in the condition known as hammer toe. In the illustrated embodiment, the surgical system 10 includes a pair of drill bits 20 and 30 and one or more absorbable pins 40.

The drill bits 20 and 30 of the surgical system 10 may be configured to define complementary features at the ends of two bones that are to be assembled with and fused to one another. Drill bit 20 is a male drill bit, which is configured to define a recess, or receptacle, in the end of a bone. Drill bit 20 may include an elongated guide 22 at its leading end, oriented along the drill bit 20's axis of rotation. The elongated guide 22 may be configured for insertion into a guide hole (not shown in FIG. 1) that has been defined in the bone (not shown in FIG. 1) with which the drill bit 20 is used and to hold the drill bit 20 in place and/or stabilize the drill bit 20 as it defines a recess (not shown in FIG. 1) in the end of the bone. A cutter 24 of the drill bit 20 includes one or more somewhat axially oriented, generally outwardly (from the axis of rotation) facing cutting elements arranged circumferentially around the axis of rotation of the drill bit 20. In the depicted embodiment, the cutter 24 includes four (4) cutting elements. Behind the cutter 24, the drill bit 20 also includes a shaft 26 oriented along its axis of rotation. The shaft 26 is configured to couple the drill bit 20 to a drill (not shown); for example, a surgical drill.

Drill bit 30 is a female drill bit, and is configured to define a protruding feature at the end of a bone. A leading end of the drill bit 30 may comprise an elongated guide 32 oriented along the axis of rotation of the drill bit 30. The elongated guide 32 may be configured for insertion into a guide hole (not shown in FIG. 1) that has been defined in the bone (not shown in FIG. 1) with which the drill bit 30 is used and to hold the drill bit 30 in place and/or stabilize the drill bit 30 as it defines a protruding feature (not shown in FIG. 1) at the end of the bone. A cutter 34 of the drill bit 30 includes one or more somewhat axially oriented, inwardly (toward the axis of rotation) facing cutting elements arranged circumferentially around the axis of rotation of the drill bit 30. FIG. 1 illustrates an embodiment in which the cutter 34 includes five (5) cutting elements. A shaft 36, which is configured to couple the drill bit 30 to a drill (not shown), such as a surgical drill, is located behind the cutter 34 and is oriented along the axis of rotation of the drill bit 30.

The absorbable pin 40 comprises an elongated element configured to be disposed within a channel formed in opposed ends of two bones that are to be fused together in an end-to-end relationship. A diameter of the absorbable pin 40 may be substantially the same as the diameter of a channel within which the absorbable pin 40 is configured to be received. More specifically, a diameter of the absorbable pin 40 may be configured to retain the absorbable pin 40 within the channel (e.g., by an interference fit, etc.) and to prevent the assembled bones from sliding apart from one another.

The material from which the absorbable pin 40 is formed is configured to be dissolved by a subject's body over time. The time that it takes the absorbable material of the absorbable pin 40 to fully dissolve after it has been introduced into the body of a subject may correspond roughly to or slightly exceed the amount of time it takes a pair of bones that have been surgically treated in accordance with teachings of this disclosure to heal or fuse to one another (e.g., about four weeks or longer, about two months or longer, about four months or longer, up to about six months, etc.). In some embodiments, the absorbable material may include or be used in conjunction with an osteogenic material. The material of the Suitable materials for the absorbable pin 40 include, but are not limited to, a polyglycolide, polyglycolic acid (PGA), a polylactide, polylactic acid (PLA) or any other biocompatible absorbable material that may provide desired amounts of structural support and a desired rate of degradation, or dissolution.

The absorbable pin 40 may also be configured to provide a desired amount of structural support to two assembled bones while they heal or fuse to one another. The structural characteristics of the absorbable pin 40 (e.g., its strength, rigidity, flexibility, etc.) may be a function of its dimensions and the material or materials from which it is formed. In some embodiments, the absorbable pin 40 may have sufficient rigidity to maintain an assembled relationship between a pair of bones that have been oriented in an end-to-end relationship. The strength of the absorbable pin 40 may enable it to withstand forces are applied against the bones within which it resides (e.g., forces that are incurred by toes during walking, etc.). In addition, the absorbable pin 40 may be sufficiently flexible and resilient to recover from flexion between the assembled bones as forces are applied against the bones (e.g., forces that are incurred by toes during walking, etc.).

Reference is now turned to FIGS. 2-7, which depict a surgical procedure for fusing two bones together. As shown in FIGS. 4 and 5, two bones $P_m$ and $P_p$, in this case, a medial phalange and a proximal phalange, respectively, are separated from one another at a joint between them. As the bones $P_m$ and $P_p$ are separated, their adjacent, or opposed, ends, which were previously part of a joint between the bones $P_m$ and $P_p$, are exposed.

As illustrated by FIGS. 2 and 4, a guide hole 28, 38 may be formed in a newly exposed end of each bone $P_m$, $P_p$, respectively. Each guide hole 38 may be formed using a surgical drill (not shown) with a standard bit 15 of desired diameter (e.g., 1 mm, 2 mm, etc.). Each guide hole 28, 38 may extend along a length of its respective bone $P_m$, $P_p$, and be positioned substantially centrally within the bone $P_m$, $P_p$, (e.g., along an approximate axis of the bone $P_m$, $P_p$, etc.).

Each guide hole 28, 38 may receive a guide 22, 32 (FIG. 1) of a drill bit 20, 30 FIGS. 3 and 5). As shown in FIGS. 3 and 5, each drill bit 20, 30 may be used in conjunction with a surgical drill (not shown) to define a corresponding feature at the end of one of the bones $P_m$, $P_p$. As illustrated by FIG. 3, drill bit 30—the female drill bit—may define a protruding feature 39 at an end of bone $P_p$. Likewise, drill bit 20—the male drill bit—may define a recess 29, or a receptacle, at (or in) the end of bone $P_m$. The protruding feature 39 and the recess 29 may be configured complementary to one another, which may enable them to mate with each other.

FIG. 6 illustrates mating between an embodiment of a protruding feature 39 and an embodiment of a recess 29 that are complementarily configured. As shown in FIG. 6, the protruding feature 39 at the end of bone $P_p$ is inserted into the recess 29 in the end of bone $P_m$. As these complementary features engage one another, the two bones $P_m$ and $P_p$ assume an assembled relationship. In some cases, engagement between the protruding feature 39 and the recess 29 may be sufficient to hold the bones $P_m$ and $P_p$ in the assembled relationship. In other embodiments, a pin or a similar feature may be desired or required to maintain the assembled relationship between the bones $P_m$ and $P_p$.

As shown in FIG. 7, an absorbable pin 40 may be inserted into the guide holes 28 and 38 in, or longitudinal channels extending at least partially through, the bones $P_m$ and $P_p$, which holes or channels may define a continuous channel when the bones $P_m$ and $P_p$ are properly assembled with each other. Insertion of the absorbable pin 40 may occur after the bones $P_m$ and $P_p$ have been assembled with each other. Alternatively, as illustrated by FIG. 7, the absorbable pin 40 may be inserted into one of the guide holes 28, 38 before the bones $P_m$ and $P_p$ are assembled, and then inserted into the other guide hole 38, 28 as the bones $P_m$ and $P_p$ are assembled. In such an embodiment, the absorbable pin 40 may ensure that the bones $P_m$ and $P_p$ are properly oriented relative to one another and, thus, properly placed in the assembled relationship.

As the bones $P_m$ and $P_p$ remain in the assembled relationship over time, they begin to fuse together, as illustrated by FIG. 8. In addition, the absorbable pin 40 begins to dissolve. When the healing process is substantially complete, as depicted by FIG. 9, the absorbable pin 40 (FIGS. 1, 7 and 8) has totally dissolved and the previously separate, adjacent bones $P_m$ and $P_p$ have fused to form a single bone. Since the body dissolves, or absorbs, the absorbable pin 40 over time, there is nothing left to remove the bone once fusion has progressed to an extent where the fused bone is self-supporting. Thus, the absorbable pin 40 eliminates the need for a follow-up surgical procedure to remove a pin.

While the procedure depicted by FIGS. 2-7 is a specific surgical procedure for correcting hammer toe by fusing adjacent bones to one another in an end-to-end arrangement, a variety of surgical procedures for fusing two bones or two pieces of a bone (e.g., a broken bone, a bone that has been cut (e.g., to adjust its length, etc.), etc.) to one another are within the scope of this disclosure.

Although the foregoing description contains many specifics, these should not be construed as limiting the scope of any of the claims, but merely as providing illustrations of some embodiments of the disclosed subject matter. Features from different embodiments may be employed in combination. Other embodiments of the disclosed subject matter may be devised which do not depart from the scope of any of the claims. The scope of each claim is, therefore, indicated and limited only by its plain language and the legal equivalents thereto, rather than by the foregoing description. All additions, deletions and modifications to the disclosed subject matter that fall within the meaning and scope of any of the claims are to be embraced thereby.

What is claimed:

1. A surgical system for straightening a toe, comprising:
   a male drill bit for forming:
      a cylindrical recess in an end of a first bone on a first side of an interphalangeal joint; and
      a first longitudinal channel concentric with the recess and extending from the recess into the first bone from the recess,
      the male drill bit including a shaft and a male cutting element comprising a plurality of blades, the plurality of blades of the male cutting element defining a cylindrical shape having an outer cutting diameter upon rotation of the male drill bit about the shaft;
   a female drill bit for forming:
      a cylindrical protrusion at an end of a second bone on a second side of the interphalangeal joint, the cylindrical protrusion configured to mate with the cylindrical recess at the interphalangeal joint to define an assembled relationship comprising a fixed interphalangeal joint; and
      a second longitudinal channel concentric with the protrusion and extending through the protrusion and into the second bone, the second longitudinal channel configured align with the first longitudinal channel when the cylindrical protrusion is inserted in the cylindrical recess,
      the female drill bit including a shaft and a female cutting element comprising a plurality of blades, the plurality of blades of the female cutting element defining a cylindrical shape having an inner cutting diameter upon rotation of the female drill bit about the shaft, the inner cutting diameter being the same as or smaller than the outer cutting diameter of the male cutting element of the male drill bit; and
   a pin configured to extend through and to be retained by the first longitudinal channel and the second longitudinal channel and to extend across the fixed interphalangeal joint to further hold the first bone and the second bone in the assembled relationship.

2. The surgical system of claim 1, wherein the male drill bit is configured to define the cylindrical recess and the first longitudinal channel concurrently.

3. The surgical system of claim 1, wherein the female drill bit is configured to define the cylindrical protrusion and the second longitudinal channel concurrently.

4. The surgical system of claim 1, wherein the male drill bit and the female drill bit are reusable.

5. The surgical system of claim 4, wherein the male drill bit and the female drill bit are configured to be sterilized.

6. The surgical system of claim 1, wherein the pin comprises a synthetic absorbable material.

7. The surgical system of claim 6, wherein the synthetic absorbable material comprises an osteogenic material.

8. The surgical system of claim 7, wherein the synthetic absorbable material comprises a polyglycolic acid or a polylactic acid.

9. A kit for toe straightening surgery, comprising:
   a male drill bit for forming:
      a cylindrical recess in an end of a first bone on a first side of an interphalangeal joint; and
      a first longitudinal channel concentric with the recess and extending from the recess into the first bone from the recess,
      the male drill bit including a shaft and a male cutting element comprising a plurality of blades, the plurality of blades of the male cutting element defining a cylindrical shape having an outer cutting diameter upon rotation of the male drill bit about the shaft;
   a female drill bit for forming:
      a cylindrical protrusion at an end of a second bone on a second side of the interphalangeal joint, the cylindrical protrusion configured to mate with the cylindrical recess at the interphalangeal joint to define an assembled relationship comprising a fixed interphalangeal joint; and
      a second longitudinal channel concentric with the protrusion and extending through the protrusion and into the second bone, the second longitudinal channel configured align with the first longitudinal channel when the cylindrical protrusion is inserted in the cylindrical recess, the female drill bit including a shaft and a female cutting element comprising a plurality of blades, the plurality of blades of the female cutting element defining a cylindrical shape having an inner cutting diameter upon rotation of the female drill bit about the shaft, the inner cutting diameter being the same as or smaller than the outer cutting diameter of the male cutting element of the male drill bit; and a plurality of single-use pins, each pin of the single-use pins:

configured to extend through and to be retained by the first longitudinal channel and the second longitudinal channel and to extend across the fixed interphalangeal joint to further secure the first bone and the second bone in the assembled relationship.

10. The kit of claim 9, wherein each pin of the plurality of single-use pins is configured to hold the first bone and the second bone in an assembled relationship.

11. The kit of claim 9, wherein the male drill bit and the female drill bit are reusable.

12. A method for straightening a toe, comprising:
accessing an interphalangeal joint;
separating bones on opposite sides of the interphalangeal joint;
imparting opposed ends of the bones with mating features that are configured to fixedly secure the bones together in a manner that defines a fixed interphalangeal joint, the mating feature comprising cooperating male and female cylinders;
defining channels through at least portions of the lengths of the bones, the channels configured to define a continuous channel through the bones when the mating features of the bones engage each other to define an assembled relationship between the bones;
placing the bones in the assembled relationship; and
inserting a pin into the channels or the continuous channel.

13. The method of claim 12, wherein inserting the pin comprises inserting an osteogenic absorbable pin.

14. The method of claim 12, wherein inserting the pin eliminates a need for a follow-up surgical procedure.

15. The method of claim 12, wherein imparting opposed ends of the bones with mating features comprises defining a recess in an end of a first bone of the bones and defining a protruding feature complementary to the recess in an end of a second bone of the bones.

16. The method of claim 15, wherein defining the recess and defining the protruding feature comprise drilling the recess and the protruding feature.

17. The method of claim 12, wherein imparting opposed ends of the bones with mating features and defining channels through at least portions of the lengths of the bones includes concurrently forming a mating feature at an end of the first bone and defining a first channel through at least a portion of a length of the first bone.

18. The method of claim 17, wherein imparting opposed ends of the bones with mating features and defining channels through at least portions of the lengths of the bones includes concurrently forming a mating feature at an end of the second bone and defining a second channel through at least a portion of the length of the second bone.

19. The method of claim 18, wherein defining channels through at least portions of the lengths of the bones comprises defining a channel completely through a distal-most bone of the bones, the channel opening to a distal end of the distal-most bone.

20. The method of claim 12, wherein inserting the pin follows placing the bones in the assembled relationship.

* * * * *